US005780429A

United States Patent [19]

Wainwright

[11] Patent Number: 5,780,429

[45] Date of Patent: Jul. 14, 1998

[54] ANTI-LPS FACTOR FROM HORSESHOE CRABS AND METHODS OF USE

[75] Inventor: Norman R. Wainwright, Falmouth, Mass.

[73] Assignee: Marine Biological Laboratory, Woods Hole, Mass.

[21] Appl. No.: 577,464

[22] Filed: Dec. 22, 1995

[51] Int. Cl.$^6$ .................... A61K 38/00

[52] U.S. Cl. .................... 514/12; 530/350; 530/857; 424/70.1

[58] Field of Search .................... 424/70.1; 514/12, 514/21; 530/350, 857

[56] References Cited

U.S. PATENT DOCUMENTS

| | | | |
|---|---|---|---|
| 5,378,731 | 1/1995 | Andrews et al. | 514/552 |
| 5,510,120 | 4/1996 | Jones et al. | 424/499 |
| 5,594,113 | 1/1997 | Wainwright | 530/395 |

FOREIGN PATENT DOCUMENTS

| | | |
|---|---|---|
| WO 89/12644 | 12/1989 | WIPO . |
| WO 92/03535 | 3/1992 | WIPO . |
| 9220715 | 11/1992 | WIPO . |
| WO 92/20715 | 11/1992 | WIPO . |
| WO 94/25476 | 11/1994 | WIPO . |

OTHER PUBLICATIONS

Kloczewiak et al. (1994) *J. Infect. Dis.* 170:1490–1497.

Kuppermann et al. (1994) *J. Infect. Dis.* 170:630–635.

Warren et al. (1992) *Infect. Immun.* 60:2506–2513.

Wainwright, et al. In: *Cellular and Molecular Aspects of Endotoxin Reactions,* Nowotny A., Spitzer, J.J. and Ziegler, E.J., eds., Amsterdam: Elsevier Science 315–324 (1990).

Desch et al. (1989) *Infect. Immun.* 57:1612–1614.

Morita et al. (1985) *J. Biochem.* 97:1611–1620.

Alpert et al. (1992) *J. Infect. Dis.* 165:494–500.

Garcia et al. (1994) *Crit. Care Med.* 22:8 1211–1218.

Saladino et al. (1994) *Circ. Shock* 42:104–110.

Kupperman et al. (1992) *Pediatr. Res.* 3:32A.

Baldwin et al. (1991) *J. Infect Dis.* 164:542–549.

*Primary Examiner*—Cecilia J. Tsang
*Assistant Examiner*—C. Delacroix-Muirheid
*Attorney, Agent, or Firm*—Hale and Dorr LLP

[57] ABSTRACT

This invention is directed to pharmaceutical and cosmetic compositions comprising anti-lipopolysaccharide (anti-LPS) factor proteins derived from horseshoe crabs, either in the native form or produced by recombinant means. The pharmaceutical formulations, which may include anti-LPS factor proteins alone or in combination with other antimicrobials, may be used in the treatment of gram-negative bacterial infections, endotoxemia, septic shock, gram-positive bacterial infections, and yeast infections. The anti-LPS factor protein-containing pharmaceuticals can be formulated for systemic or topical administration. They may also be used to control mold growth. Anti-LPS factor proteins can be used in cosmetic compositions or skin or hair preparations as antimicrobial preservatives, either alone or in combination with conventional preservatives, to prevent or control the growth of bacteria, yeast and mold.

6 Claims, 5 Drawing Sheets

```
GAT GGT ATT TGG ACT CAA TTG ATT TTT ACT TTG GTT AAT AAT TTG GCT
Asp Gly Ile Trp Thr Gln Leu Ile Phe Thr Leu Val Asn Asn Leu Ala
 1               5                  10                  15

ACT TTG TGG CAA TCT GGT GAT TTT CAA TTT TTG GAT CAT GAA TGT CAT
Thr Leu Trp Gln Ser Gly Asp Phe Gln Phe Leu Asp His Glu Cys His
            20                  25                  30

TAT AGA ATT AAA CCA ACT TTT AGA AGA TTG AAA TGG AAA TAT AAA GGT
Tyr Arg Ile Lys Pro Thr Phe Arg Arg Leu Lys Trp Lys Tyr Lys Gly
        35                  40                  45

AAA TTT TGG TGT CCA TCT TGG ACT TCT ATT ACT GGT AGA GCT ACT AAA
Lys Phe Trp Cys Pro Ser Trp Thr Ser Ile Thr Gly Arg Ala Thr Lys
    50                  55                  60

TCT TCT AGA TCT GGT GCT GTT GAA CAT TCT GTT AGA AAT TTT GTT GGT
Ser Ser Arg Ser Gly Ala Val Glu His Ser Val Arg Asn Phe Val Gly
65                  70                  75                  80

CAA GCT AAA TCT TCT GGT TTG ATT ACT CAA AGA CAA GCT GAA CAA TTT
Gln Ala Lys Ser Ser Gly Leu Ile Thr Gln Arg Gln Ala Glu Gln Phe
                85                  90                  95

ATT TCT CAA TAT AAT
Ile Ser Gln Tyr Asn
           100
```

FIG.1

ANTI-LPS FACTOR FROM HORSESHOE CRABS AND METHODS OF USE

FIELD OF THE INVENTION

The present invention is in the field of antibacterial pharmaceutical compositions and in the field of antimicrobial preservatives.

BACKGROUND OF THE INVENTION

Endotoxins are high molecular weight lipopolysaccharide complexes that are released when gram-negative bacteria are disrupted, such as occurs during antibiotic therapy when bacteria are lysed. Endotoxins, an outer wall constituent of the gram-negative bacteria, are potent stimulators of the inflammatory response which produce pyrogenic reactions upon intravenous administration. While an inflammatory response that is measured is beneficial in fighting infection, it can be damaging to the host when it is uncontrolled, as is the case with septic shock.

Bacterial endotoxin is a complex of lipid, carbohydrate and protein. It is characterized by an overall negative charge, heat stability and high molecular weight. Highly purified endotoxin is a lipopolysaccharide (LPS) that does not contain protein. It is the lipopolysaccharide component of bacterial endotoxins that causes endotoxemia and septic shock.

LPS consists of three distinct chemical regions: (1) the phospholipid moiety (lipid A), which is the innermost region of LPS and the source of toxicity; (2) an intermediate core polysaccharide; and (3) an outermost O-specific polysaccharide side chain which is responsible for the antigenicity of the endotoxin.

LPS from gram-negative bacteria induces the release of mediators from host inflammatory cells which may ultimately result in disseminated intravascular coagulation (DIC), adult respiratory distress syndrome (ARDS), cardiac dysfunction, organ failure, liver failure (hepatobiliary dysfunction), brain failure (CNS dysfunction), renal failure, multi-organ failure and shock.

While there are many antibiotics used against gram-negative bacterial infections, due to the increase in antibiotic resistant bacteria, there is still a need to identify effective antibiotics.

SUMMARY OF THE INVENTION

This invention is directed to pharmaceutical compositions and uses of anti-lipopolysaccharide (anti-LPS) factor proteins derived from horseshoe crabs, either in the native form or produced by recombinant or synthetic means. The pharmaceutical formulations may be used in the treatment of gram-negative bacterial infections, endotoxemia and septic shock. The invention is further directed to pharmaceutical compositions and uses of anti-LPS factor proteins against infections by gram-positive bacteria. The invention is also directed to pharmaceutical compositions and uses of anti-LPS factor proteins as an antimycotic agent. The pharmaceutical compositions may include anti-LPS factor proteins alone or in combination with other known antibiotics or antimycotic agents.

Finally, this invention is also directed to the use of anti-LPS factor proteins as antimicrobial preservatives, either alone or in combination with conventional preservatives, in cosmetics or skin or hair preparations to prevent or control the growth of bacteria, yeast and mold.

BRIEF DESCRIPTION OF THE DRAWINGS

FIG. 1 is the nucleotide sequence (SEQ. ID NO:1) for the gene encoding LALF, Limulus anti-LPS factor, with the derived amino acid sequence (SEQ. ID NO:2).

DETAILED DESCRIPTION OF THE INVENTION

Figure 2A:
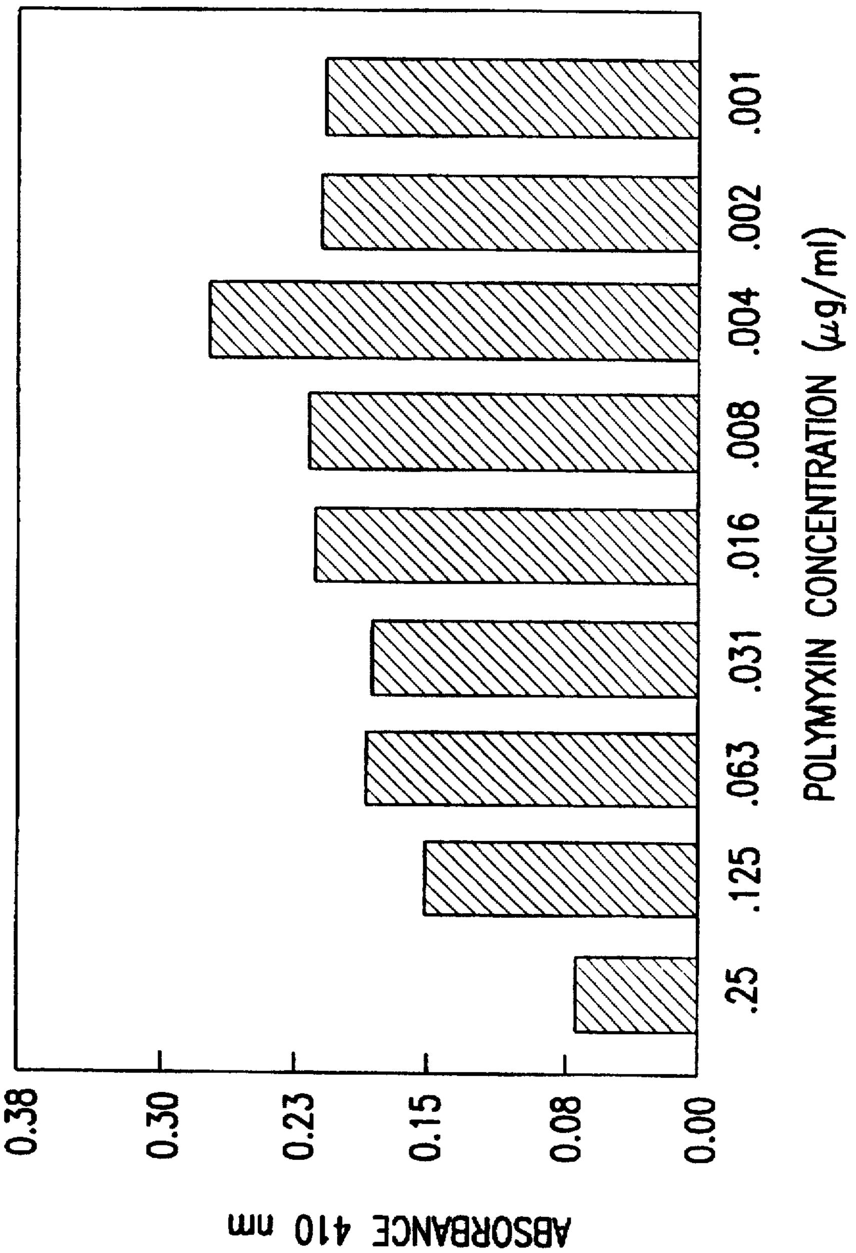
FIG. 2(A) is a graphic representation of the inhibitory effect of increasing concentrations of the antibiotic polymyxin B (PMB) on the growth of the gram-negative bacteria *E. coli*.

This invention is directed, in part, to the use of anti-LPS factor proteins in the preparation of new and more potent antibiotics for treating bacterial and yeast infections. It has been discovered that anti-LPS factor proteins from horseshoe crabs produce a synergism in controlling gram-negative bacterial infections when combined with antibiotics that are known to be effective against gram-negative infections. New antibiotics for treating gram-negative bacterial infections are therefore made by combining anti-LPS factor proteins with antibiotics that are known to be effective in controlling gram-negative bacterial infections.

It has also been discovered that anti-LPS factor proteins are effective antibiotics for treating gram-positive bacterial infections and yeast infections. Anti-LPS factor proteins also control the growth of mold. In addition to being effective against these microbes when administered alone, anti-LPS factor proteins can also be combined with one or more known antimicrobials that are effective against gram-positive bacteria, yeast and mold.

The new anti-LPS factor protein-based therapeutics of the present invention can be formulated for systemic or topical administration.

Finally, anti-LPS factor proteins are useful antimicrobial preservatives, either alone or in combination with conventional preservatives, in cosmetics or skin and hair preparations where they prevent and control the growth of a broad spectrum of bacteria, yeast and mold for extended periods of time.

I. Definitions.

As used in this application, the following words or phrases have the meanings specified:

"LPS" means lipopolysaccharide which is used synonymously with the word "endotoxin."

"Anti-LPS factor" means a protein isolated from any species of horseshoe crab, that is capable of binding to and neutralizing the biological activity of bacterial endotoxins.

"Anti-LPS factor protein" means (1) anti-LPS factor derived from any species of horseshoe crab; (2) biologically active fragments of anti-LPS factor; or (3) biologically active polypeptide analogs of anti-LPS factor, each of which may be either recombinant, nonrecombinant, or synthetic.

"Synthetic analogs means any polypeptide which has substantially the same amino acid sequence as anti-LPS factor and is chemically synthesized.

"Endotoxin" means a toxin from a gram-negative bacterium which is pyrogenic.

II. Anti-lipopolysaccharide (anti-LPS) factor proteins.

Anti-LPS factor proteins for use in the present invention may be isolated from amebocytes of any horseshoe crab. For example, any of the four known species of horseshoe crabs could be used. These species are: *Limulus polyphemus, Tachypleus gigas, Tachypleus tridentatus* and *Carcinoscropius rotundicauda.* Especially preferred among these is *Limulus polyphemus,* the horseshoe crab which is found along the North American coast. The methods for isolating and purifying native or endogenous anti-LPS factor are well known. WO 92/20715, WO 89/12644, and Kloczewiak, M., et al., *J. Infectious Diseases,* Vol. 170, 1490–97(1994).

A preferred anti-LPS factor protein for use in this invention is the anti-LPS factor produced by *Limulus polyphemus,* called Limulus anti-LPS factor or LALF. LALF may be used in the various embodiments of this invention as a purified endogenous protein and as a recombinant protein. LALF has been isolated, sequenced and expressed as a recombinant protein in *Saccharomyces cerevisiae,* as described in Kuppermann, N., et al., *J. Infect. Dis.,* Vol 170, 630–5 (1994), and as described below in the Pichia expression system. Recombinant LALF expressed in Pichia has the same amino acid sequence as native LALF and is the preferred anti-LPS factor protein for use in the present invention. Both the gene sequence (SEQ ID NO.:1) and the derived amino acid sequence (SEQ ID NO:2) for LALF transcribed from yeast preferred codons in Pichia are shown in FIG. 1.

Although LALF is a preferred anti-LPS factor protein, the anti-LPS factor proteins from the other species of horseshoe crabs, which are approximately 70% homologous to LALF, may also be used in the various embodiments of the invention.

LALF is an 11.8-kDa protein that inhibits the biologic effects of endotoxin in vitro, including the gelation of Limulus amebocyte lysate (LAL). Wainwright, N. R., et al., *In: Cellular and Molecular Aspects of Endotoxin Reactions,* Nowotny A., Spitzer, J. J. and Ziegler, E. J., eds., *Amsterdam: Elsevier Science,* 315–25 (1990).

The endotoxin neutralizing activity of anti-LPS factor proteins derives from a high affinity for the lipid A portion of endotoxin. In the horseshoe crab, anti-LPS factor is part of an anti-infection pathway of aggregation where rapid degranulation and clot formation are initiated when hematocytes containing anti-LPS factor proteins are exposed to gram-negative endotoxins.

Anti-LPS factor protein has a 16 amino acid domain that is necessary for endotoxin binding and neutralization. WO 92/20715. This domain comprises the amino acid sequence of Limulus anti-LPS factor (LALF) from amino acid position 30 to amino acid position 55. Synthetic peptide analogues of LALF have been made, and the site of the activity and specific sequence needed to bind and neutralize endotoxin have been determined. Kloczewiak, M., et al., *Journal of Infectious Diseases,* Vol. 170, 1490–97 (1994).

Anti-LPS factor proteins are single chain, basic proteins that can bind to and neutralize LPS. This amphipathic protein has a rich clustering of hydrophobic amino acids at the amino terminal region and an array of basic amino acids in the central disulfide-bonded loop region. When LPS and anti-LPS factor proteins are mixed, they aggregate. The exact mode of binding is uncertain, although it is likely that the hydrophobic and cationic amino acids of anti-LPS factor proteins interact, respectively, with the fatty acid chains and the phosphate groups of the toxic lipid A region of LPS.

The endotoxin binding phenomenon by Limulus anti-LPS factor is universal. Studies have shown that LALF binds to and inactivates endotoxin from *Klebsiella pneumonias, Serratia marcescens, Salmonella enteritidis, Escherichia coli* 0113 wild type, *E. coli* rough mutant (J-5), *Salmonella abortus equi,* and Lipid A from *S. minnesota* Re 595. WO 92/20715. In these studies, the endotoxin binding protein was mixed with the endotoxins or lipid A at a ratio of 5:1 to 1,000:1 in the presence of 10 millimolar Tris buffer, pH 6–8. In all cases the measurable endotoxin activity after mixing was reduced 85% to 99.5%.

It has also been shown that anti-LPS factor proteins inhibit endotoxin-induced mitogenesis of murine splenocytes, Warren, H. S., et al., *Infect. Immun.,* Vol. 60, 2506–13 (1992); activation of human endothelial cells, Desch, C. E., et al., *Infect. Immun.,* Vol 57, 1612–4 (1992); and release of tumor necrosis factor (TNF) by human macrophages, Kuppermann, N., et al., *J. Infect. Dis.,* Vol 170, 630–5 (1994). Anti-LPS factor proteins also inhibit the growth of rough gram-negative bacteria, Morita, T., et al., *J. Biochem,* Vol. 97, 1611–20 (1985). In vivo, these proteins are protective against lethal *Escherichia coli* endotoxin challenge in rats, Wainwright, N. R., et al., supra.; and against lethal meningococcal challenge in rabbits, Alpert, G., et al., *J. Infect. Dis.,* Vol. 165, 494–500 (1992) or *E. coli,* Garcia, C. T., et al., *Crit. Care Med.* Vol 22:8, 1211–18 (1994). Recently, LALF was shown to improve survival in rabbits and rats with *E. coli* sepsis. Saladino, R., et al., *Circ. Shock,* Vol. 42, 104–10 (1994); Kuppermann, N., et al., *Pediatr. Res.,* Vol 31:32A (1992).

A rat model of endotoxemia caused by infection with an encapsulated strain of *E. coli* that is virulent in humans, was used to show that LALF at a concentration of 50 mg/kg has very potent anti-endotoxin activity in vivo. LALF blocked the lethal effects of endotoxin even after endotoxin had an opportunity to circulate and was likely to have bound to target cells. When compared with animals treated with the anti-endotoxin-monoclonal antibody HA-1A, animals treated with LALF showed significantly lower endotoxin concentrations and improved survival. HA-1A, while able to reduce circulating endotoxin concentrations, did not significantly improve survival. Kuppermann, N., et al., *J. Infect. Dis.,* Vol 170, 630–5 (1994).

Further, it has been shown that LALF given at a dose of either 2.5 or 5 mg/kg before lethal endotoxin challenge in rabbits, resulted in significant improvements in physiologic measurements and survival. LALF attenuated the toxic effects of *E. coli* endotoxin in rabbits and improved survival, even when administered after endotoxin challenge. Garcia, C., et al., *Crit. Care Med.,* Vol. 22:8, 1211–18 (1994). The administration of LALF 30 minutes after endotoxin challenge, however, had less protective activity than was obtained when it was administered before endotoxin challenge.

III. Antibiotics effective against gram-negative bacteria.

It has been discovered that anti-LPS factor proteins from horseshoe crabs potentiate, or produce a synergy, when combined with other antibiotics known to be effective against gram-negative bacterial infections. According to this invention, anti-LPS factor proteins can be used in combination with gram-negative antibiotics to produce an effective combination antibiotic for use in the treatment of gram-negative bacterial infections, endotoxemia and shock.

Gram-negative antimicrobials suitable for use in the claimed combination antibiotics include, but are not limited to, polymyxin B, ampicillin, amoxicillin, penicillin G, A tetracycline, erythromycin, spectinomycin, cefoxitin, trimethoprim-sulfamethoxazole, chloramphenicol, rifampin, minocycline, sulfonamides, nitrofurantoin, gentamicin, cefamandole, carbenicillin, ticarcillin, tobramycin, amikacin, A cephalosporin, cefoxitin, streptomycin, and clindamycin. Moreover, combinations may include more than one known gram-negative antibiotic and one or more anti-LPS factor proteins.

The discovery that anti-LPS factor proteins enhance the effectiveness of known antibiotics against gram-negative bacteria means that potent new antibiotics can be prepared using lower levels of each drug than would be necessary if either drug were administered alone. For illustration, polymyxin B (PMB) is a basic polypeptide antibiotic which has been shown to bind to, and structurally disrupt, the most toxic and biologically active component of endotoxin, Lipid A. PMB inhibits endotoxin activation of neutrophil granule release in vitro and is a potent treatment for gram-negative infections in humans. It has been shown that pretreatment with PMB is effective in preventing shock and mortality in rabbits receiving a potent dose of *E. coli* LPS. Baldwin, G., et al., *J. Infect. Dis.*, Vol. 164, 542–9 (1991). However, because of its systemic toxicity, this drug has limited use, except as a topical agent. WO 94/25476; WO 92/03535. According to this invention, a combination antibiotic comprising anti-LPS factor protein and polymyxin B, for example, can be prepared using lower concentrations of the potentially toxic polymyxin B due to the synergism produced by the inclusion of anti-LPS factor protein.

In another illustration, LALF may be combined with polymyxin B to treat septic shock caused by meningococcemia. Meningococcemia is the most common cause of septic shock in otherwise healthy children, and mortality from this condition remains high (10%) despite intensive therapy. Experiments with a meningococcal lipooligosaccharide-induced [LOS] septic shock model in rabbits, showed that pretreatment with polymyxin B alone failed to improve physiologic changes or mortality rate. Baldwin, G., et al., *J. Infect. Dis.*, Vol. 164, 542–9 (1991). By contrast, Limulus anti-LPS factor protein, LALF, significantly improved mean arterial pressure (MAP), arterial pH, serum bicarbonate concentrations, and survival even when administered 30 minutes after the lipooligosaccharide challenge. Alpert, G., *J. Infect. Dis.*, Vol. 165, 494–500 (1992). According to this invention, meningococcemia may be treated with the combination of LALF with polymyxin B.

It has been unexpectedly discovered that LALF effectively controls the growth of the gram-negative bacterium *Propionibacterium acnes*, which causes the common skin disease acne. Anti-LPS factor proteins can be used as antibiotics to treat acne either alone or in combination with other antibiotics such as tetracycline, or other medicinals such as benzoyl peroxide that are known to control *Propionibacterium acnes*. In the case of acne, anti-LPS factor proteins can be administered systemically, topically, or via simultaneous systemic and topical administration.

Therapeutic administration of the anti-LPS factor proteins alone, or in combination with gram-negative antibiotics, may be performed by methods known to those skilled in the art including topical, intravenous, intramuscular or subcutaneous routes, direct delivery into an infected body cavity by infusion, and oral or rectal administration.

A therapeutic dose of the claimed combination antibiotics is an amount that is effective to inhibit the growth of gram-negative bacteria and inhibit LPS-mediated stimulation of neutrophils and mononuclear cells. As used herein, inhibit means to inhibit at a level that is statistically significant and dose dependent. The terms "statistically significant" and "dose dependent" are well known to those skilled in the art.

In a preferred embodiment, a therapeutically effective amount of anti-LPS factor protein in the present invention is a concentration of between about 0.1 and 100 milligrams anti-LPS factor protein per kilogram of body weight. Other useful ranges include between about 0.1 and 1; 1 and 10; and 10 and 100 milligrams anti-LPS factor protein per kilogram body weight. A typical amount is between about 10 and 50 milligrams per kilogram body weight.

In addition, the amount of known gram-negative antibiotic included in the combination can be adjusted up or down based on known therapeutic doses and routine experimentation. The therapeutically effective amounts of the claimed combination antibiotics may be determined according to known methods based on the effective dosages discussed above.

IV. New antibiotics effective against gram-positive bacterial infections and new antimycotics effective against yeast infections comprising anti-LPS factor proteins.

Anti-LPS factor proteins effective against gram-positive bacteria.

Anti-LPS factor proteins have been discovered to be effective antibiotics against a wide variety of gram-positive bacteria. Thus, this invention is directed to pharmaceutical compositions containing anti-LPS factor proteins and the therapeutic use of these anti-LPS factor protein pharmaceutical compositions in the treatment of gram-positive bacterial infections. Further, anti-LPS factor proteins can be used in combination antibiotics known to be effective against gram-positive bacteria, including but not limited to penicillin G, erythromycin, A tetracycline, A cephalosporin, chloramphenicol, rifampin, aminoglycosides, vancomycin, and clindamycin. Pharmaceutical formulations or the administration of pharmaceutical compositions may include more than one anti-LPS factor protein and more than one antibiotic known to be effective against gram-positive bacteria.

A therapeutic dose of anti-LPS factor proteins either alone or in combination with known antibiotics to control gram-positive bacterial infection, is an amount that is effective to kill the gram-positive bacteria and control or inhibit the spread of the infection. An effective therapeutic dose can be determined by persons of ordinary skill in the art using known methods.

Anti-LPS factor proteins effective antimycotic agent.

It has also been discovered that anti-LPS factor proteins effectively inhibit the growth of yeast, for example, *Candida parapilosis* and *C. albicans*. It is therefore another embodiment of the present invention to use anti-LPS factor proteins as antimycotic agents either alone or in combination with other antimycotics, at a therapeutically effective dose to control yeast infections. There are many known antimycotics for treating yeast infections that can be administered in combination with anti-LPS factor proteins including but not limited to: amphotericin B, clotrimazole, flucytosine, grisefulvin, haloprogin, hydroxyslilbamidine, miconazole, nystatin, and tolnaftate. Combinations may be made of anti-LPS factor proteins and more than one other antimycotic agent.

As used herein, the therapeutic dose of the claimed anti-LPS factor protein-containing antibiotics or antimycotics is an amount that is effective to inhibit the growth of gram-positive bacteria or yeast. In an embodiment, a therapeutically effective amount of anti-LPS factor protein is a concentration of between about 0.1 and 100 milligrams anti-LPS factor protein per kilogram of body weight. Other useful ranges include between about 0.1 and 1; 1 and 10; and 10 and 100 milligrams anti-LPS factor protein per kilogram body weight. A typical amount is between about 10 and 50 milligrams per kilogram body weight.

The amount of known antibiotic or antimycotic agent included in the combination formulation can be adjusted up or down based on known therapeutic doses and routine experimentation. The therapeutically effective amounts of the claimed antibiotics and antimycotics may be determined according to known methods based on the effective dosages given above.

V. Preparation of Pharmaceutical Compositions.

The pharmaceutical compositions containing anti-LPS factor proteins of the present invention can be administered either alone or in combination with other known drugs in vivo in a pharmaceutically or veterinarilly acceptable carrier. If necessary, an adjuvant to facilitate absorbtion may be included in the formulation.

The term "carrier" as used herein means a synthetic or natural, inorganic or organic substance which is added to the endotoxin binding protein of the present invention to assist the active ingredient in reaching the location to be treated therewith and to facilitate storage, transportation and handling of the active ingredient.

Among suitable liquid carriers, there may be included aromatic hydrocarbons such as benzene, toluene, and xylene; paraffinic hydrocarbons such as mineral oil and the like; halogenated hydrocarbons such as carbon tetrachloride, chloroform, dichloroethane and the like; ketones such as acetone, methyl ethyl ketone, etc.; ethers such as dioxane, tetrahydrofuran and the like; alcohols such as methanol, propanol, ethylene glycol and the like; or dimethyl formamide, dimethylsulfoxide, water, etc. Mixtures of any number of liquid carriers are also envisioned. Dissolution of lyophilized anti-LPS factor proteins in unbuffered pyrogen-free distilled water or saline or phosphate buffered saline, can be achieved by adjusting the pH until the solution becomes water clear. For this reason, the preferred liquid carrier is pyrogen-free distilled water or saline adjusted to the appropriate pH to facilitate solubility of the anti-LPS factor proteins.

In order to enhance the effectiveness of the compound according to this invention, it is possible to use such adjuvants as given below, either singly or in combination, in accordance with the purpose of each application thereof while taking into consideration the form of their preparation and their field of application.

Exemplary adjuvants may include anionic surfactants such as alkyl sulfates, aryl sulfonates, succinates, polyethylene glycol, alkyl ether sulfates, and the like; cationic surfactants such as alkylamines, polyoxyethylene alkylamines, etc.; non-ionic surfactants such as polyoxyethylene glycol ethers, polyoxyethylene glycol esters, polyol esters and the like; and amphoteric surfactants. Encapsulation or microencapsulation of the active ingredient in liposome vesicles is also within the scope of this invention.

Examples of stabilizers, thickeners, lubricants and the like are isopropyl hydrogen-phosphate, calcium stearate, wax, casein, sodium alginate, serum albumin, other blood proteins, methylcellulose, carboxymethylcellulose, gum arabic, etc. It should be kept in mind that these ingredients are not limited to the recited examples.

Solutions or suspensions containing anti-LPS factor proteins may also include the following components: a sterile diluent such as water for injection, saline solution, oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple base vials made of glass or plastic.

Specific indications or diseases that may be treated by the anti-LPS factor proteins, or combination antibiotics that include anti-LPS factor proteins, include but are not limited to acne, septicemia, toxic shock, gram-negative bacterial infections, endotoxin-related arthritis, gonorrhea, periodontal disease, spinal meningitis, infections of amniotic fluid, gram-positive bacterial infections, yeast infections, and mold growth.

VI. Preparation of pharmaceutical compositions suitable for topical use comprising anti-LPS factor proteins.

In addition to systemic administration, it is also within the scope of this invention to formulate anti-LPS factor proteins into pharmaceutical compositions suitable for topical use to promote wound healing or to treat vaginal yeast infections. Topically applied anti-LPS factor proteins, either alone or in combination with other antimicrobials, can prevent or control gram-negative and gram-positive bacterial infections, yeast infections and the growth of mold.

A preferred embodiment includes topical formulations of anti-LPS factor protein alone or in combination with known antibiotics or antimycotics, suitable for application to incisions or exposed tissue for the promotion of wound healing by curing or preventing bacterial or yeast infections. In another embodiment, anti-LPS factor proteins are formulated into suppositories to treat vaginal yeast infections.

There are no limitations as to the type of wound or other traumata that can be treated, and these include: first, second and third degree burns, especially second and third degree; epidermal and internal surgical incisions, including those of cosmetic surgery; wounds, including lacerations, incisions, and penetrations; and epidermal ulcers including decubital (bed sores), diabetic, dental, hemophiliac, and varicose.

Anti-LPS factor protein compositions are applied to burns in the form of a sterile irrigant, preferably in combination with a physiological saline solution, or in the form of ointments or suspensions, preferably in combination with purified collagen. The compositions may also be impregnated into transdermal patches, plasters, bandages, or sterile implants preferably in a liquid or semi-liquid form.

A therapeutically effective dose of anti-LPS factor protein is a dose that inhibits the growth of bacteria, yeast, and mold when applied topically. The range of acceptable doses of anti-LPS factor proteins for topical application includes between about 0.01 and 10 weight percent. Where known antibiotic or antimycotic agents are combined with anti-LPS factor proteins, their concentration can be varied up or down based on the range of known clinically acceptable concentrations for these drugs.

Initial dosing of anti-LPS factor protein either alone or in combination with other agents, should be delivered topically to the therapeutic site at a concentration of about 0.5 weight percent. This dose can be thereafter adjusted up or down in line with clinical experience. Continued application or periodic reapplication of the compositions is indicated. The clinician will be expected to modify the dosage in accordance with clinical experience.

In a preferred embodiment, anti-LPS factor proteins are topically applied at a concentration of between about 0.01 and 10 weight percent in a pharmaceutically acceptable carrier. Other preferred embodiments include application at concentrations of between about 0.1 and 1; 1 and 2; 2 and 5; 5 and 7; and 7 and 10 weight percent; most preferred is between about 1 and 2 weight percent.

VII. Use of anti-LPS factor proteins as an antimicrobial preservative either alone or in combination with conventional preservatives.

Endotoxin is shed from living bacteria and is also released into the environment when bacteria die and decompose.

Since gram-negative bacteria are found in great numbers in air, water, and soil, bacterial endotoxin commonly contaminates raw materials and processing equipment used in the manufacturing of cosmetics and skin or hair preparations. Contamination by gram-positive bacteria, yeast and mold is also common.

This invention is also directed to a new preservative for use in topically applied cosmetics and skin or hair preparations that inhibits and controls the growth of a wide variety of microbial contaminants.

Preservatives are typically employed in cosmetics and skin and hair preparations because they are usually manufactured under clean, but non-sterile conditions. The preservatives are used to prevent the growth of microbes including bacteria, yeast and mold. A sufficient quantity of one or more preservatives is typically added so that the cosmetic or preparation resists the growth of bacteria from an experimental inoculation for extended periods of time.

There is a need for new, effective preservatives in the cosmetic industry. Many consumers have been sensitized to currently available preservatives and have developed allergic reactions. It has been discovered that relatively low doses of anti-LPS factor proteins act as preservatives by preventing or suppressing the growth of a broad range of gram-negative and gram-positive bacteria as well as some yeasts and mold, for extended periods of time.

Anti-LPS factor proteins can be used alone or in combination with known preservatives in topically applied cosmetics, or skin or hair preparations. The cosmetics and skin or hair preparations may be powders, creams, lotions, or gels. Some preservatives that are typically used are imidazolidinyl urea, sodium hydroxy methylglycinate, diazolidinyl urea, glyoxyl diureide, chlorphenesin, methylparaben, an ester of p-hydroxy-benzoic acid, chloromethyl-thiazoline, methyl-isothiazoline, phenyoxyethanol, hexetidine, chloro-hexydingluconate, and the parabens: butyl, isobutyl, methyl, propyl, and isopropyl. Another commercially available preservative that may be used in combination with anti-LPS factor protein is known as PHENONIP™ which is a practically colorless, viscous, liquid mixture of phenoxyethanol, methylparaben, ethylparaben, propylparaben, and butylparaben available from Nipa Laboratories, Inc., Wilmington, Del.

The anti-LPS factor proteins appear to act as potentiators of preservatives used in cosmetics and skin and hair preparations. By using anti-LPS factor protein as a preservative in a cosmetic or a skin or hair preparation, the concentration of previously known preservatives may be reduced or eliminated. Thus, anti-LPS factor proteins not only act as preservatives, they also minimize the antigenicity of the cosmetic or lotion by replacing commonly used preservatives to which some consumers have become sensitized. Anti-LPS factor proteins also neutralize endotoxin which is another source of antigenicity.

The amount of anti-LPS factor protein that may be used as a preservative varies from between about 0.005 and 5 weight percent of the cosmetic or lotion. It is preferred that the lowest effective amount of anti-LPS factor protein be used to prevent sensitization of the user to anti-LPS factor protein. This amount can be determined by routine experimentation and it will vary according to whether anti-LPS factor protein is used alone or in combination with other preservatives. The amount used will also depend upon the formulation of the cosmetic or lotion and the storage conditions.

In a preferred embodiment, anti-LPS factor protein is present as a preservative at a concentration of between about 0.005 and 0.01; 0.01 and 0.1; 0.1 and 1; 1 and 2; or 2 and 5 weight percent with the most preferred being between about 0.01 and 1 weight percent.

Various aspects of the invention are illustrated in the following examples to aid in understanding the invention, which is not intended to be limiting.

EXAMPLES

Example 1: Expression and Purification of Recombinant LALF in Pichia

Fermentation: LALF protein expression in Pichia:

The gene encoding LALF is shown in FIG. 1, SEQ ID NO:1. The LALF gene has been cloned into the Pichia pPIC9K vector as an in-frame fusion with the alpha mating factor secretion signal. The gene encoding LALF (SEQ ID NO:1) was synthesized by Genosys, Inc. The design of the synthetic gene was based on the sequence of the deduced amino acid sequence from the native LALF protein sequence. Codons were chosen which optimize expression in yeast (based on *Saccharomyces cerevisiae*). The amino terminal sequence, N-Asp-Gly-Ile-Trp-Thr, is ideally suited for correct cleavage of the yeast alpha mating factor secretion signal. The gene was modified using PCR mutagenesis to incorporate 5' cloning sites that juxtapose the codon for the N-terminal Asp residue found in the mature LALF with the codon for the last amino acid residue in the yeast alpha mating factor secretion signal. Kex2-like protease cleavage of the fusion protein generates a secreted, mature, native form of the LALF protein.

Expression is driven by the Pichia methanol-inducible AOX1 promoter. The *Saccharomyces cerevisiae* a-factor prepro leader peptide, present on the expressed protein as an N-terminal fusion, targets the protein for secretion into the media and is cleaved off in the process. Expression of the protein of interest is induced by growing the His+ recombinant strain in methanol-containing media. Scorer, C. A., et al, *Gene*, Vol. 136, 111–19 (1993); Scorer, C. A., et al., *Bio/Technology*, Vol. 12, 181–4 (1994).

Filtration: The media containing the secreted protein, is clarified by hollow fiber diafiltration (0.45 micron, A/G Technologies) at high flow rate (1–5 liters/min.) and low back pressure (5–10 psi).

Ultrafiltration: The first purification step is achieved by collecting the filtrate from a 30,000 Dalton cut-off tangential flow ultrafiltration membrane cassette. This filtrate is concentrated by a 8,000 dalton cut-off membrane, achieving a rapid size exclusion.

Chromatography: Concentrated 8–30,000 dalton crude LALF is loaded onto a cation exchange column. After extensive washing with Phosphate Buffered Saline (PBS), a linear gradient of NaCl, O-1 Molar in PBS is used to elute the purified LALF. The eluate may be desalted by ultrafiltration, or if necessary, a second step purification by reversed-phase chromatography may be performed. The high salt peak is loaded directly on the column and eluted with a linear gradient of 0–50% isopropanol, 0.1% Trifluoroacetic acid. It is preferable to freeze, lyophilize and store the purified LALF at 20° C. until used.

Example 2: The Combination of LALF with Polymyxin B Produces a Synergistic Effect Against Gram-negative Bacteria

*E. coli* cells were cultured overnight at 37° C. in Difco Luria Broth (LB). Aliquots were diluted 1:100 in fresh LB (control). LB plus polymyxin B (PMB) was serially diluted from 0.25 micrograms/ml to 0.001 micrograms/ml. LB plus LALF was formulated at concentrations from 20 to 0.07 micrograms/ml. Combinations of polymyxin B and LALF were formulated as indicated in FIG. 2. Optical density was recorded at 410 nm during the course of the experiment.

FIG. 2A shows the inhibitory effect of polymyxin B by itself on *E. coli* at concentrations ranging from 0.001 to 0.25 micrograms/ml. As one dilutes the antibiotic, the growth of the *E. coli*, as measured by optical density, increases. A concentration of 0.06 micrograms PMB/ml was chosen for the subsequent LALF combination experiments shown in FIG. 2B because 0.06 micrograms PMB is only slightly effective (approximately 20% inhibition of growth) against *E. coli.*

Figure 2B:
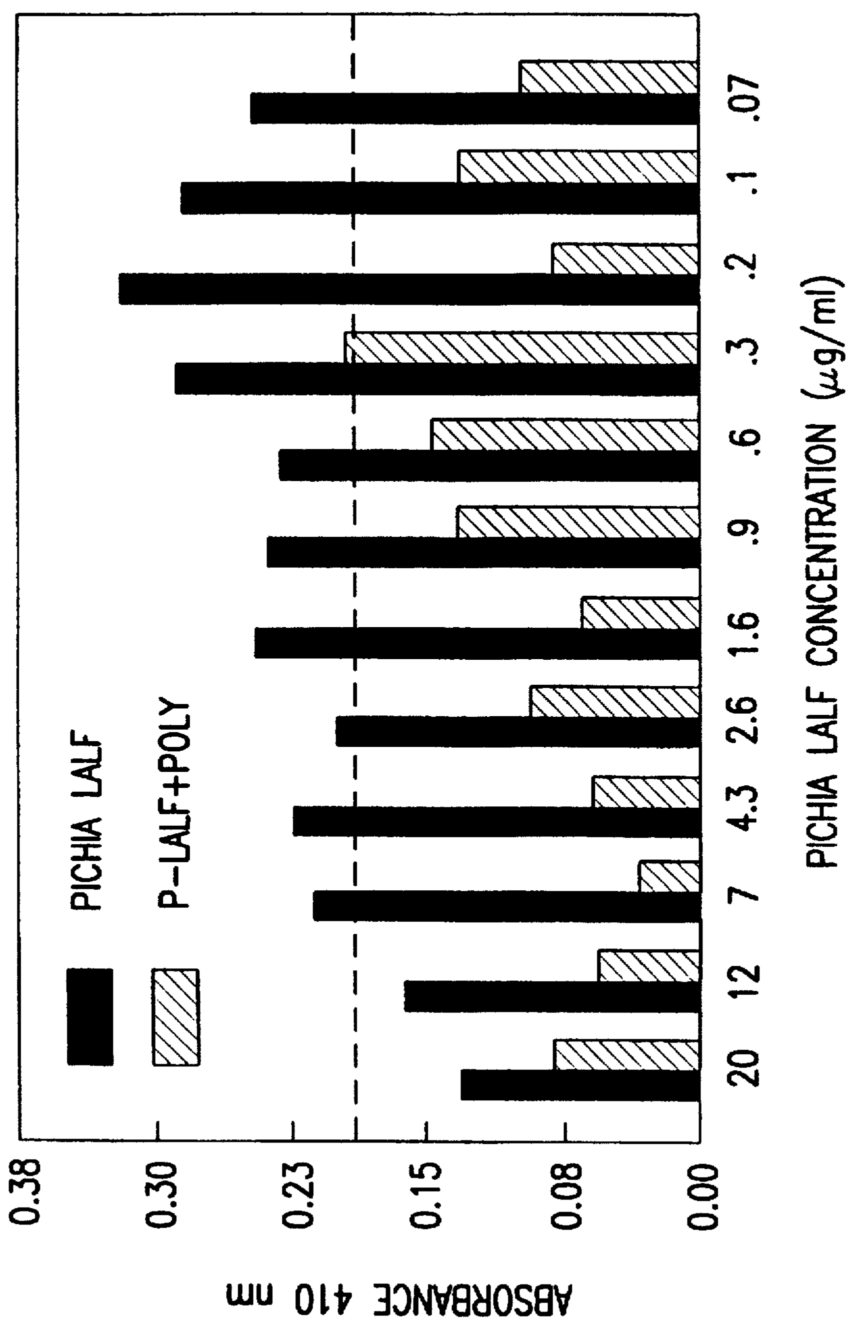
FIG. 2(B) is a graphic comparison of the inhibitory effect of increasing concentrations of LALF on the growth of *E. coli* with the effect of a combination antibiotic containing 0.06 micrograms/ml polymyxin B and increasing concentrations of LALF.
Figure 3:
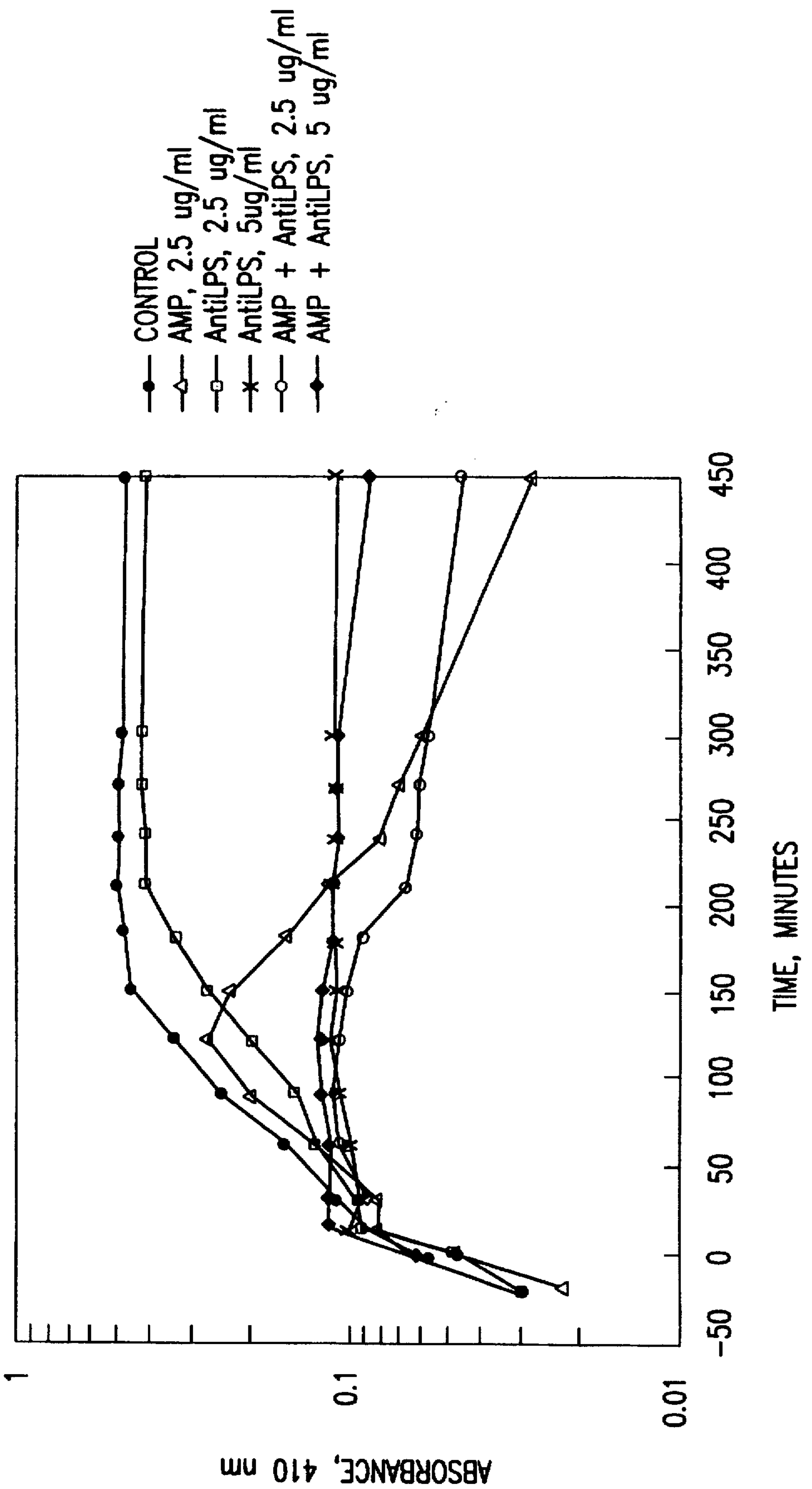
FIG. 3 is a graphic comparison of the inhibitory effects on the growth of *E. coli* of (1) 2.5 micrograms/ml ampicillin, (2) 2.5 micrograms/ml LALF, (3) 5.0 micrograms/ml LALF, (4) 2.5 micrograms/ml ampicillin plus 2.5 micrograms/ml LALF, (5) and 2.5 micrograms/ml ampicillin plus 5 micrograms/ml LALF.

FIG. 2B shows that the addition of LALF to PMB produces a synergistic antibiotic effect on the growth of gram-negative bacteria. The concentration of PMB is held constant at 0.06 micrograms/ml throughout the experiment. The level of growth of *E. coli* allowed by 0.06 micrograms/ml PMB alone is shown by the dashed line. The antibiotic effect of LALF alone at concentrations ranging from 20 to 0.07 micrograms/ml, is indicated by the solid black bars.

To test the potentiation of the antibiotic effect of PMB by LALF, a combination antibiotic was formed comprising 0.06 micrograms/ml polymyxin B and various concentrations of LALF ranging from 20 to 0.07 micrograms/ml. The level of growth of *E. coli* in the combined antibiotic PMB/LALF is indicated by the cross-hatched bars. The results show that LALF across a broad range of concentrations produces a synergistic effect when combined with 0.06 micrograms/ml PMB.

Example 3: The Combination of LALF with Ampicillin Produces a Synergistic Effect Against Gram-negative Bacteria It has also been discovered that LALF produces an in vitro synergism in controlling gram-negative bacteria when combined with the antibiotic ampicillin, a well known semisynthetic, acid-resistant form of penicillin.

*E. coli* cells were cultured overnight at 37° C. in Difco Luria Broth (LB). Aliquots were diluted 1:100 in fresh LB (control). Test samples consisted of LB plus ampicillin at 2.5 micrograms/ml; LB plus LALF at 2.5 and 5 micrograms/ml; and combinations of 2.5 micrograms/ml ampicillin and either 2.5 or 5.0 micrograms/ml LALF. Optical density was recorded at 410 nm during the course of the experiment.

The combination of 2.5 micrograms/ml LALF and 2.5 micrograms/ml ampicillin, produced a synergistic effect in inhibiting the growth of *E. coli.*

Example 4: LALF is an Effective Antibiotic Against *Propionibacterium acnes*

The antibiotic effect of recombinant LALF was tested against *Propionibacterium acnes,* the bacterium that causes acne, using the zone inhibition method. Petri dishes were filled with sterile nutrient agar following standard microbiological procedures. The nutrient agar-filled dishes were allowed to cool and harden before being inoculated with test bacteria. Using a sterile swab, the surface of the petri dishes were inoculated with a culture of *Propionibacterium acnes,* ATCC No. 11827, that had grown overnight at 37° C.

Sterile filter paper discs (4 mm, Whatman) were treated with 10 microliters of aqueous solutions of (1) recombinant LALF at a concentration of 1 mg/ml: the test sample; (2) benzoyl peroxide at a concentration of 0.05%: the positive control; or (3) sterile saline: the negative control. Benzoyl peroxide serves as a positive control because it is known to inhibit the growth of *Propionibacterium acnes.*

The treated filter paper discs were incubated overnight at 37° C. Incubation in LALF produced a zone of inhibition around the test sample having a diameter of 4–5 mm. Incubation in benzoyl peroxide (the positive control) produced a zone of inhibition having a diameter of 10–11 mm. The negative control treated with sterile saline had no zone of inhibition. These results show that recombinant LALF is an effective antibiotic against *Propionibacterium acnes.*

Example 5: LALF is an Effective Antibiotic Against Gram-Positive Bacteria

Uncharacterized gram-positive bacteria isolated from marine organisms, were cultured overnight at 37° C. in Difco Luria Broth (LB). Aliquots were diluted 1:100 in fresh LB (control). Test samples consisted of LB plus LALF at 2.5 and 5.0 micrograms/ml. Optical density was recorded at 410 nm during the course of the experiment to monitor the growth of gram-positive bacteria.

Figure 4:
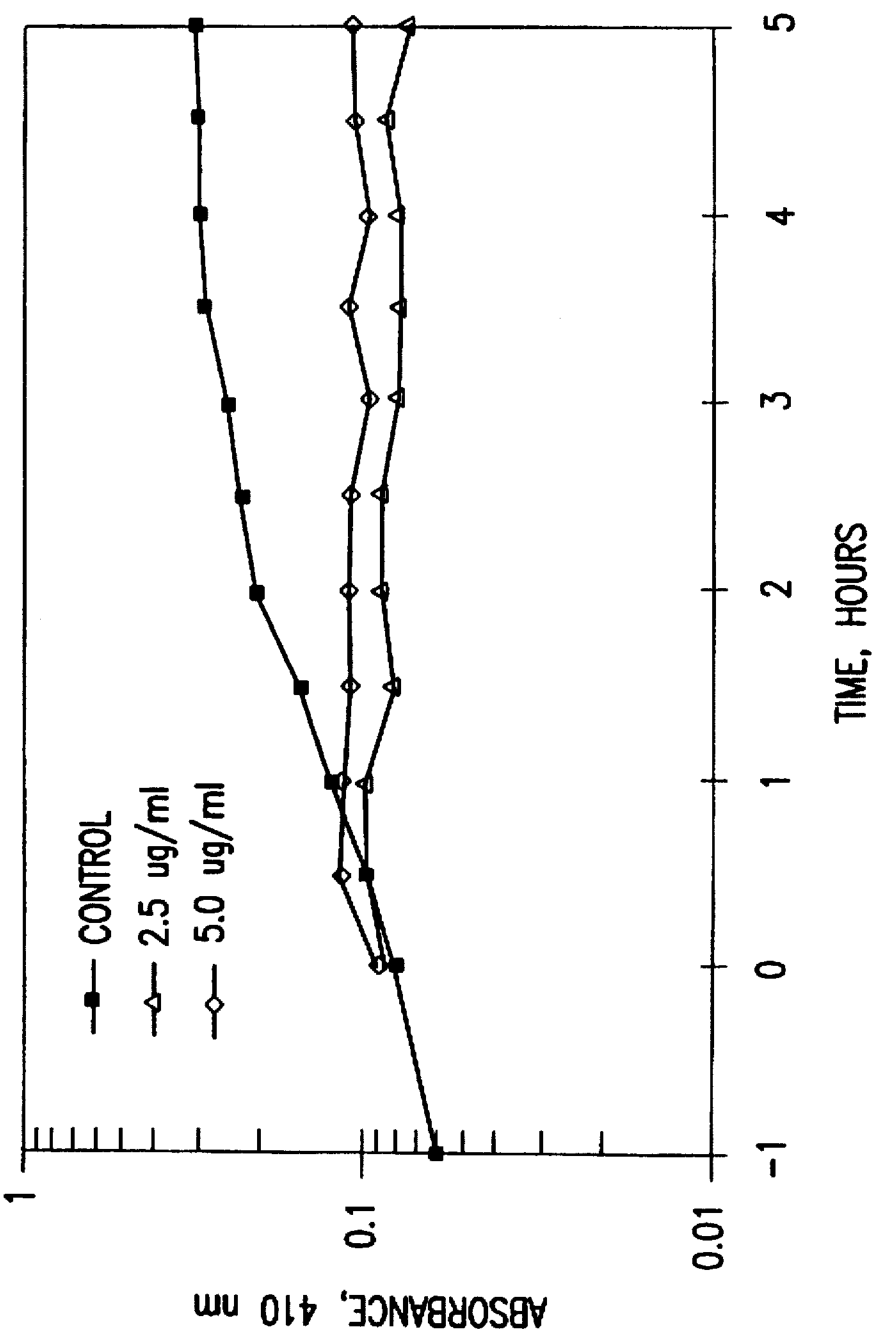
FIG. 4 is a graphic representation of the inhibitory effect of 2.5 and 5 micrograms/ml LALF on uncharacterized gram-positive bacteria isolated from marine organisms.

FIG. 4 shows that LALF at concentrations of either 2.5 or 5 micrograms/ml is effective at inhibiting the growth of gram-positive bacteria over the five hour course of the experiment.

Example 6: LALF is an Effective Antimicrobial Preservative in Topically Applied Cosmetics and Lotions Against a Broad Spectrum of Microbes Challenge microorganisms were prepared as pools of related organisms which were grown in the appropriate medium. The cell number was quantitated by serial dilution:

TABLE I

| Pool 1 | Pool 2 | Pool 3 |
|---|---|---|
| (Gram-negative)<br>*Escherischia coli*<br>*Enterobacter gergorise*<br>*E agglomerans*<br>*Klebsiella pneumoniae* | (Gram-negative)<br>*Pseudomonas cepacia*<br>*P. putida*<br>*P. statzeri*<br>*P. aeruginoss* | (Gram-positive)<br>*Staph. epidermidis*<br>*Staph. aeureus* |
| **Pool 4** | **Pool 5** | |
| (Yeast)<br>*Candida parapilosis*<br>*C. albicans* | (Mold)<br>*Aspergillus niger* | |

An oil in water emulsion was prepared comprised of the following ingredients:

TABLE II

| | |
|---|---|
| Cetyl alcohol (fatty alcohol) | 1.65 g |
| Glycerol stearate | 1.65 |
| Ariacel 165 (surfactant) | 6.60 |
| Dehydag wax (surfactant) | 1.10 |
| Softisan 378 (triglyceride/oil) | .50 |
| Silicone 200/100 | .40 |
| Cetiol LC | 3.60 |
| Tween 40 (emulsifier) | .66 |
| Ariacel 40 | .44 |
| DI Water (distilled) | 74.00 |
| 1.3 Btgly | 6.00 |
| EDTA (chelator) | .10 |

For control experiments, the formula was prepared as above. To test anti-LPS antibiotic activity, LALF was added to the emulsion to achieve a concentration of 0.01 weight percent, with appropriate adjustment of the DI Water.

Control and anti-LPS emulsions were spiked with $10^8$ viable cells from each of the five microorganism pools. Cell number was quantitated by serial dilution. The number of viable microbial cells was determined by plate count at the time of the initial spike, and at weekly intervals up to 8 weeks. The number of viable cells was determined by taking an aliquot from the sample, diluting it and culturing it so that colonies arising from individual cells could be counted. After obtaining an aliquot for testing at Week 3, microbes were re-spiked to initial levels as indicated in Table III.

TABLE III

| | | | | LALF Emulsion | | | | | |
|---|---|---|---|---|---|---|---|---|---|
| Pools | (spike) Initial | Wk 1 | Wk 2 | (spike) Wk 3 | Wk 4 | Wk 5 | Wk 6 | Wk 7 | Wk 8 |
| Results: | | | | | | | | | |
| 1 | 6.0 | <1.0 | <1.0 | <1.0 | 2.7 | <1.0 | <1.0 | <1.0 | <1.0 |
| 2 | 6.0 | <1.0 | <1.0 | <1.0 | <1.0 | <1.0 | <1.0 | <1.0 | <1.0 |
| 3 | 6.0 | 3.2 | <1.0 | <1.0 | 3.0 | <1.0 | <1.0 | <1.0 | <1.0 |
| 4 | 6.0 | <1.0 | <1.0 | <1.0 | 3.0 | <1.0 | <1.0 | 1.7 | <1.0 |
| 5 | 5.0 | 5.0 | 3.0 | 2.6 | 2.8 | 2.7 | <1.0 | 3.0 | 2.7 |
| Control: | | | | | | | | | |
| 1 | 6.0 | 6.0 | 3.0 | <1.0 | 6.0 | 6.0 | | 6.0 | 6.0 |
| 2 | 6.0 | 6.0 | 2.0 | <1.0 | 6.0 | 6.0 | | 6.0 | 6.0 |
| 3 | 6.0 | 6.0 | 2.3 | 2.6 | 6.0 | 6.0 | | 6.0 | 6.0 |
| 4 | 6.0 | 6.0 | 1.7 | <1.0 | 6.0 | 6.0 | | 6.0 | 6.0 |
| 5 | 5.0 | 5.0 | 5.0 | 5.0 | 5.0 | 5.0 | | 5.0 | 5.0 |

The results of this example show that LALF is an effective antimicrobial preservative in topically applied cosmetics and lotions. LALF at a relatively low concentration of 0.01 percent (weight/volume), was able to kill a wide spectrum of bacteria and prevent their regrowth over an eight week period, even when the emulsion was re-spiked with bacteria at three weeks. LALF was also effective at killing and preventing the regrowth of the yeasts *Candida parapilosis* and *albicans*. While LALF was less effective against the mold *Aspergillus niger* than against bacteria and yeast, it nonetheless limited the growth of mold. LALF therefore acted as a mycostatic agent with respect to mold while it more ressively controls the growth of bacteria and yeast.

Although the foregoing invention has been described in some detail by way of illustration and example for purposes of clarity and understanding, it will be obvious to one of skill in the art that certain changes and modifications may be practiced within the scope of the appended claims.

What is claimed is:

1. A preservative for use in a topically applied cosmetic or skin or hair preparation, comprising one or more anti-LPS factor proteins, wherein said anti-LPS factor protein is present in an amount sufficient to inhibit the growth of bacteria, yeast and mold.

2. The preservative according to claim 1 further comprising a commercially available preservative.

3. The preservative according to claim 2 wherein the commercially available preservative is selected from the group consisting of imidazolidinyl urea, sodium hydroxy methylglycinate, diazolidinyl urea, glyoxyl diureide, chlorphenesin, methylparaben, an ester of p-hydroxybenzoic acid, chloro-methyl-thiazoline, methyl isothiazoline, phenyoxyethanol, hexetidine, chlorohexydingluconate, butylparaben, isobutylparaben, methylparaben, propylparaben, and isopropylparaben.

4. The method of preserving a cosmetic or skin or hair preparation, comprising adding an effective amount of one or more anti-LPS factor proteins as a broad spectrum antimicrobial preservative, either alone or in combination with one or more preservatives.

5. A method of minimizing the antigencity of a cosmetic or skin or hair preparation comprising replacing a sensitive commercially available preservative with one or more anti-LPS factor proteins.

6. The method of claim 5 wherein the anti-LPS factor protein neutralizes endotoxin.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 303 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

```
GATGGTATTT GGACTCAATT GATTTTTACT TTGGTTAATA ATTTGGCTAC TTTGTGGCAA    60
TCTGGTGATT TTCAATTTTT GGATCATGAA TGTCATTATA GAATTAAACC AACTTTTAGA   120
AGATTGAAAT GGAAATATAA AGGTAAATTT TGGTGTCCAT CTTGGACTTC TATTACTGGT   180
AGAGCTACTA AATCTTCTAG ATCTGGTGCT GTTGAACATT CTGTTAGAAA TTTTGTTGGT   240
CAAGCTAAAT CTTCTGGTTT GATTACTCAA AGACAAGCTG AACAATTTAT TTCTCAATAT   300
AAT                                                                 303
```

( 2 ) INFORMATION FOR SEQ ID NO:2:

( i ) SEQUENCE CHARACTERISTICS:
( A ) LENGTH: 101 amino acids
( B ) TYPE: amino acid
( C ) STRANDEDNESS: single
( D ) TOPOLOGY: linear ( i i ) MOLECULE TYPE: peptide -continued ( x i ) SEQUENCE DESCRIPTION: SEQ ID NO:2:

| | | | | | | | | | | | | | | |
|---|---|---|---|---|---|---|---|---|---|---|---|---|---|---|
| Asp | Gly | Ile | Trp | Thr | Gln | Leu | Ile | Phe | Thr | Leu | Val | Asn | Asn | Leu |
| | | | | 5 | | | | | 10 | | | | | 15 |
| Ala | Thr | Leu | Trp | Gln | Ser | Gly | Asp | Phe | Gln | Phe | Leu | Asp | His | Glu |
| | | | | 20 | | | | | 25 | | | | | 30 |
| Cys | His | Tyr | Arg | Ile | Lys | Pro | Thr | Phe | Arg | Arg | Leu | Lys | Trp | Lys |
| | | | | 35 | | | | | 40 | | | | | 45 |
| Tyr | Lys | Gly | Lys | Phe | Trp | Cys | Pro | Ser | Trp | Thr | Ser | Ile | Thr | Gly |
| | | | | 50 | | | | | 55 | | | | | 60 |
| Arg | Ala | Thr | Lys | Ser | Ser | Arg | Ser | Gly | Ala | Val | Glu | His | Ser | Val |
| | | | | 65 | | | | | 70 | | | | | 75 |
| Arg | Asn | Phe | Val | Gly | Gln | Ala | Lys | Ser | Ser | Gly | Leu | Ile | Thr | Gln |
| | | | | 80 | | | | | 85 | | | | | 90 |
| Arg | Gln | Ala | Glu | Gln | Phe | Ile | Ser | Gln | Tyr | Asn | | | | |
| | | | | 95 | | | | | 100 | | | | | |